United States Patent [19]
Poziomek et al.

[11] 3,972,783
[45] Aug. 3, 1976

[54] METHOD OF TESTING A TOXIC AGENT ALARM WITH A NONTOXIC SIMULANT OF METHANESULFONYL HALIDE

[75] Inventors: Edward J. Poziomek, Bel Air; Eleanor V. Crabtree, Towson, both of Md.

[73] Assignee: The United States of America as represented by the Secretary of the Army, Washington, D.C.

[22] Filed: Oct. 8, 1974

[21] Appl. No.: 513,016

[52] U.S. Cl. ............................... 204/1 T; 252/408
[51] Int. Cl.² ............................................. B01K 1/00
[58] Field of Search ............ 204/1 T, 1 B, 1 N, 1 F; 252/408

[56] References Cited
UNITED STATES PATENTS

| 2,865,719 | 12/1958 | Kramer | 252/408 X |
| 3,470,071 | 9/1969 | Vertes et al. | 204/1 T |
| 3,844,905 | 10/1974 | Epstein | 252/408 X |

OTHER PUBLICATIONS

Iverson, Chem. Abs., 74, Abs. No. 107526, (1971).
Saville, Analyst, 82, pp. 269–274, (1957).
Green et al., J. Chem. Soc., 1956, pp. 3887–3892, (1956).
Spoliti et al., Chem. Abs., 66, Abs. No. 64907, (1967).

*Primary Examiner*—Edward A. Miller
*Attorney, Agent, or Firm*—Nathan Edelberg; Kenneth P. Van Wyck

[57] ABSTRACT

A method of testing; i.e., challenging a V and G toxic agent alarm through use of a simulant compound having no significant toxicity to insure alarm sensitivity and function.

4 Claims, No Drawings

METHOD OF TESTING A TOXIC AGENT ALARM WITH A NONTOXIC SIMULANT OF METHANESULFONYL HALIDE

DEDICATORY CLAUSE

The invention described herein may be manufactured, used, and licensed by or for the Government for governmental purposes without the payment to us of any royalty thereon.

DESCRIPTION OF THE INVENTION

Our invention relates to a method of challenging a V and G toxic agent alarm, such as disclosed in U.S. Pat. application Ser. No. 768,560 filed Oct. 16, 1968, through use of a simulant compound which has no significant toxicity.

The dissemination of toxic compounds such as hydrogen cyanide, hydrogen sulfide, and chemical warfare agents of the class known as G and V agents into the atmosphere at industrial plants and in warfare necessitates monitoring the atmosphere for the presence of low concentrations of air contaminants, such as 0.2 $\times 10^{-6}$ to 0.4 $\times 10^{-6}$ grams of contaminant toxic compound per liter of air. The device disclosed in the aforementioned U.S. Pat. application Ser. No. 768,560 satisfies this need. With the development of the aforementioned monitoring device arose the problem of insuring reliability of function and sensitivity of the device without resorting to the use of the toxic material themselves, with their inherent hazards and transport restrictions. A simulant compound was thus sought that would have no significant toxicity and which would nevertheless mimic the toxic G class agents, such as those disclosed in U.S. Pat. Nos. 2,926,072 and 2,929,791, and challenge the agent alarm function under anticipated operating conditions. Our invention was conceived and reduced to practice to satisfy the need for a material having no significant physiological activity; i.e., toxicity to function as a simulant for G agents, particularly GB, to be used in a method of challenging an agent alarm.

A primary object of our invention is to provide a method whereby a toxic V and G agent alarm can be challenged by a compound which has no significant physiological activity; i.e., toxicity, but which mimics the G agents, particularly GB, to insure reliability of function and sensitivity of the alarm under anticipated operating conditions.

Other objects of our invention will be obvious from the specification hereinafter set forth.

The standardized V and G toxic agent electrical cell alarm and method disclosed in U.S. Pat. application Ser. No. 768,560 is based upon the capability of a silver electrode to detect submicrogram quantities of cyanide ions. G agents are absorbed into a cell electrolyte and are directly reacted with an oxime, resulting in the rapid generation of cyanide ions. The cyanide ions, in turn, diffuse throughout the electrolyte and are detected by the silver electrode. V agents are not detected directly by the oxime reaction, but they are converted to the corresponding G analogues by means of chemical reaction with an impregnate in a conversion prefilter. The G agents and analogues react with an oxime; e.g., isonitrosobenzoyl acetone (IBA) to liberate cyanide ions and subsequently produce the electrochemical reaction

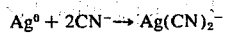

at the silver electrode.

Each decade change in cyanide concentration in the alarm cell electrolyte produces a 120mV change in potential, enabling G and V agent detection and quantitative estimation. The mechanics of the oxime reaction are as follows:

1. Formation of the oxime anion

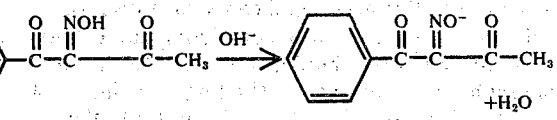

2. O-phosphorylation of the oxime anion

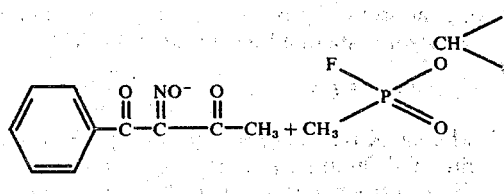

3. Rapid cleavage of the oxime phosphonate

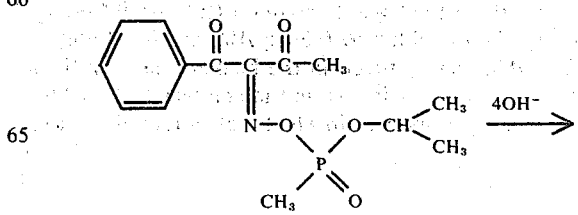

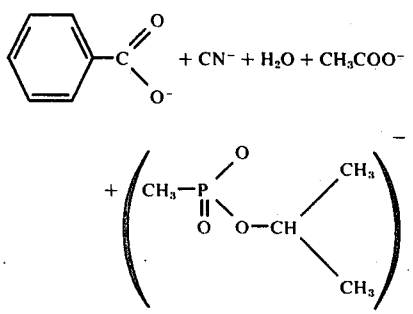

Silver nitrate and potassium fluoridate are impregnated in the conversion filter to convert V agents to their G analogues, such as phosphonofluoridates, to react with the oxime; G agents being nonreactive with the chemical conversion filter composition. While not a part of this invention, the impregnating of the conversion filter can be accomplished by the process disclosed in the aforementioned U.S. Pat. application Ser. No. 768,560.

To solve the above problem of providing a simulant for G agents, particularly GB, in the testing of the agent alarm, applicants found it necessary to provide a simulant compound that (1) had a volatility similar to that of GB, for use with current agent vapor generator and sampling devices and (2) were chemically reactive with the reagent solution of the alarm system so as to give the same measurable resultant product as that produced using G agents.

In response to this need, applicants have discovered that the commerically available compounds methanesulfonyl chloride (boiling point of 161°C) and methanesulfonyl fluoride (boiling point of 123°–124°C) have volatilities closely similar to that of GB (boiling point of 147°C, Merck Index) and a demonstrated chemical reactivity with the alarm reagent solution, when tested in a beaker cell agent alarm simulator, of that of GB, as shown by the production of the same measurable reaction product. The response noted for the methanesulfonyl fluoride more closely resembled the GB response, and is therefore the preferred simulant compound.

The following examples further illustrate the use of methanesulfonyl fluoride and methanesulfonyl chloride as simulant compounds for G agents in our novel method of challenging V and G agent alarms and should not be construed to limit our invention in any way.

The materials used in beaker cell response tests of the simulant compounds were methanesulfonyl fluoride (b.p. 123° – 124°C) and methanesulfonyl chloride (b.p. 161°C) obtained in fresh white label grade from Distillation Products, and GB (96 percent purity) stabilized b.p. 147°C (Merck Index).

The tests were performed in a beaker cell with exactly 1.0 ml of the "agent" solution (2 × 10⁻⁴M in dry dioxane) being added to 0.30 g IBA in 40 ml borate buffer while being stirred in the beaker cell. The final concentration in each case in the cell was $5 \times 10^{-6}M$. The resulting responses in electrical potential for the simulant compounds and GB are summarized in the following table.

| Compound | Background | Response, mV ½ min | 1 min | 2 min | 3 min |
|---|---|---|---|---|---|
| $CH_3SO_2Cl$ | 1 | 58 | 57 | 56 | |
| $CH_3SO_2Cl$ | 4 | 59 | 55 | 54 | |
| $CH_3SO_2Cl$ | 4 | 70 | 67 | 65 | |
| $CH_3SO_2Cl$ | 2 | 57 | 54 | | |
| $CH_3SO_2F$ | 3 | 26 | 48 | 58 | 60 |
| $CH_3SO_2F$ | 2 | 20 | 46 | 55 | 57 |
| GB | 3 | 40 | 52 | 52 | |
| GB | 3 | 40 | 50 | 50 | |
| GB | 3 | 46 | 53 | 52 | |
| GB | 3 | 36 | 52 | 52 | |

An important criterion for cell acceptance is a 21mV cell response within 2 minutes at an agent B concentration of 0.2 to 0.25 μg/l.

The experimental results have indicated that approximately 2.4 times more simulant compound than G agent is required to effect an equivalent beaker cell response. An acceptable 21mV cell response within 2 minutes at an agent B concentration of 0.23μg./liter thus requires a simulant compound concentration of 0.5 to 0.6μg/l to meet the above mentioned criterion for practical agent alarm cell response.

Applicants having disclosed their invention, obvious modification of the present invention will be apparent to those skilled in the related chemical art and thus desire to be limited only by the scope of the appended claims.

What is claimed is:

1. A method of testing; i.e., challenging a toxic G and V agent alarm for the detection of toxic G agents by using a simulant compound for said G agents which has no significant toxicity, said alarm including an electrochemical cell with a silver electrode for the detection of $CN^-$ ions, said cell having an electrolyte including an oxime for reaction with phosphonofluoridates, G agents and analogues thereof, whereby $CN^-$ ions are generated, said alarm further including $AgNO_3$ and KF for th conversion of V agents to G analogues, comprising the steps of providing an air sample containing said simulant compound having the formula

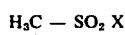

$$H_3C - SO_2 X$$

wherein X is a halogen of the group consisting of chlorine and fluorine, passing said simulant compound to the electrochemical cell and reacting simulant compound with the electrolyte of the electrochemical cell of the alarm to produce $CN^-$ ions in the cell electrolyte, reacting the $CN^-$ ions at the silver electrode of the electrochemical cell to produce a change in potential, and monitoring the change in potential to determine the alarm challenge.

2. The method of claim 1 wherein X is fluorine.

3. The method of claim 1 wherein the simulant compound is present in a concentration approximately 2.4 times the concentration level of toxic G agent being simulated in the agent alarm test.

4. The method of claim 3 wherein the simulant compound is present in a concentration of 0.5 to 0.6μg/liter of air.

* * * * *